United States Patent [19]
Godfrey

[11] Patent Number: 5,897,891
[45] Date of Patent: Apr. 27, 1999

[54] FLAVORFUL ZINC COMPOSITIONS FOR ORAL USE INCORPORATING COPPER

[76] Inventor: John C. Godfrey, 1649 Old Welsh Rd., Huntingdon, Pa. 19006

[21] Appl. No.: 08/751,608

[22] Filed: Nov. 18, 1996

[51] Int. Cl.$^6$ .............................. A23L 1/304; A23L 1/305
[52] U.S. Cl. ................................ 426/74; 426/656; 426/3; 426/4; 426/5; 426/660; 424/48; 424/49; 424/55; 514/494; 514/499
[58] Field of Search .................................. 426/74, 656, 3, 426/4, 5, 660; 424/48, 49, 55; 514/494, 499

[56] References Cited

U.S. PATENT DOCUMENTS

| | | |
|---|---|---|
| Re. 33,465 | 11/1990 | Eby, III . |
| 4,684,528 | 8/1987 | Godfrey . |
| 4,758,439 | 7/1988 | Godfrey ..................................... 426/74 |
| 4,837,219 | 6/1989 | Hutterer . |
| 5,075,116 | 12/1991 | LaHaye et al. . |
| 5,132,113 | 7/1992 | Lucá ........................................ 426/74 |
| 5,569,477 | 10/1996 | Nesbitt ...................................... 426/74 |

FOREIGN PATENT DOCUMENTS

| | | |
|---|---|---|
| 2 674 755 A1 | 10/1992 | France . |
| 2 022 998 | 12/1979 | United Kingdom . |

OTHER PUBLICATIONS

Anon., "Zinc" *The Medical Letter* (Jun. 30, 1978) vol. 20, No. 13, Issue 508, pp. 57–59.

P. Beaumont, "Zinc and Macular Degeneration" (letter) *Arch. Ophthalmol.* (Aug. 1993) vol. 111, No. 8, p. 1023.

N. Boukaïba et al, "A Physiological Amount of Zinc Supplementation: Effects on Nutritional, Lipid, and Thymic Status in an Elderly Population" *Am.J.Clin.Nutr.* (1993) vol. 57, No. 4, pp. 566–572.

I. Bremner, "The Toxicity of Cadmium, Zinc and Molybdenum and their Effects on Copper Metabolism" *Proc.Nutr.Soc.* (1979) vol. 38, pp. 235–242.

G.J. Brewer et al, "Treatment of Wilson's Disease with Zinc: III Prevention of Reaccumulation of Hepatic Copper" *J.Lab.Clin.Med.* (May 1987) vol. 109, No. 5, pp. 526–531.

R.K. Chandra, "Excessive Intake of Zinc Impairs Immune Responses" *JAMA* (Sep. 21, 1984) vol. 252, No. 11, pp. 1443–1446.

S.F. Crouse et al, "Zinc Ingestion and Lipoprotein Values in Sedentary and Endurance–Trained Men" *JAMA* (Aug. 10, 1984) vol. 252, No. 6, pp. 785–787.

S.C. Cunnane, *Zinc: Clinical and Biochemical Significance* CRC Press, Inc., Boca Raton, FL (1988) pp. 22, 61, 62, 06, 108, 115–117.

M.D. Festa et al, "Effect of Zinc Intake on Copper Excretion and Retention in Men" *Am.J.Clin.Nutr.* (Feb. 1985) vol. 41, pp. 285–292.

S.M. Filteau et al, "Zinc & Immunity" (letter) *Nutrition Reviews* (Aug. 1986) vol. 44, No. 8, pp. 283–284.

J.H. Freeland–Graves et al, "Effect of Zinc Supplementation on Plasma High–Density Lipoprotein Cholesterol and Zinc" *Am.J.Clin.Nutr.* (May 1982) vol. 35, pp. 988–992.

J.S. Goodwin et al, "Relationship Between Zinc Intake, Physical Activity, and Blood Levels of High–Density Lipoprotein Cholesterol in a Healthy Elderly Population" *Metabolism* (Jun. 1985) vol. 34, No. 6, pp. 519–523.

P.L. Hooper et al, "Zinc Lowers High–Density Lipoprotein–Cholesterol Levels" *JAMA* (Oct. 24/31, 1980) vol. 244, No. 17, pp. 1960–1961.

Z.A. Karcioglu et al, *Zinc & Copper in Medicine* Charles C. Thomas, Publisher, Springfield, IL (1980) pp. 229, 351, 352, 622.

L.M. Klevay, "Dietary Copper: A Powerful Determinant of Cholesterolemia" *Med. Hypotheses* (1987) vol. 24, pp. 111–119.

L.M. Klevay, "The Influence of Copper and Zinc on the Occurrence of Ischemic Heart Disease" *J.Env.Path. Tox.* (1980) vol. 4–2, No. 3, pp. 281–287.

L.M. Klevay, "Ischemia Heart Disease: Updating the Zinc/Copper Hypothesis" *Am.Coll.Nutr.* (1982) vol. 5 (monograph G9), pp. 61–67.

P.L. Leung et al, "The Changes of Metabolism Balance of Zinc and Copper in Gastric Juice with Widely Varying Dietary Zinc Intake" *Chem. Abstract* 119:269610d re *Biol.Trace.Elem.Res.* (1993) vol. 39, No. 1, pp. 33–39.

I. Lombeck, "The Clinical Significance of Trace Elements in Childhood" *Ergeb.Inn.Med.Kinderheilkd.* (1980) vol. 44, pp. 1, 3, 13, 19, 26–27, 30, 31, 33 and 34.

H.C. Lukaski et al, "Physical Training and Copper, Iron and Zinc Status of Swimmers" *Am.J.Clin.Nutr.* (1990) vol. 51, pp. 1093–1099.

C.J. McClain et al, "Copper Toxicity in Wilson's Disease: An Absorbing Problem" (editorial) *J.Lab.Clin.Med.* (Mar. 1988) vol. 111, No. 3, pp. 261–262.

W.P. Patterson et al, "Zinc–Induced Copper Deficiency: Megamineral Sideroblastic Anemia" *Ann.Int.Med.* (Sep. 1985) vol. 103, No. 3, pp. 385–386.

C.C. Pfeiffer et al, "Effect of Chronic Zinc Intoxication on Copper Levels, Blood Formation, and Polyamines" *Orthomolecular Psychiatry* (1980) vol. 9, No. 2, pp. 79–89.

A.S. Prasad et al, "Hypocupremia Induced by Zinc Therapy in Adults" *JAMA* (Nov. 10, 1978) vol. 240, No. 20, pp. 2166–2168.

H. Sandstead, "Zinc Interference with Copper Metabolism" *JAMA* (Nov. 10, 1978) vol. 240, No. 20, pp. 2188–2189.

(List continued on next page.)

*Primary Examiner*—Chhaya D. Sayala
*Attorney, Agent, or Firm*—Breiner & Breiner

[57] ABSTRACT

Compositions for oral use containing a zinc compound, a copper compound, an amino acid and a base material are described. The compositions provide for slow release of zinc ions upon dissolution in the mouth to thereby achieve beneficial therapeutic effects from the zinc ions. The amino acid is selected to provide the composition with a palatable taste and no after-taste. The copper compound provides copper ions which serve to counterbalance a large intake of zinc as is present upon prolonged oral use of the composition.

16 Claims, No Drawings

OTHER PUBLICATIONS

H.H. Sandstead, "Zinc Requirements, the Recommended Dietary Allowance and the Reference Dose" *Scand.J.Work.Environ.Health* (1993) vol. 19, Supp. 1, pp. 128–131.

H.H. Sandstead, "Zinc–Copper Interaction Provides a Novel and Apparently Effective Alternative Therapy for Wilson's Disease" *J.Lab.Clin.Med.* (May 1987) vol. 109, No. 5, pp. 521–522.

H.H. Sandstead, "Zinc, Copper and Cholesterol" (letter) *JAMA* (Apr. 17, 1981) vol. 245, No. 15, p. 1528.

B. Sandström et al, "Acrodermatitis Enteropathica, Zinc Metabolism, Copper Status, and Immune Function" *Arch.Pediatr.Adolesc.Med.* (Sep. 1994) vol. 148, No. 9, pp. 980–985.

C.L. Trempe, "Zinc and Macular Degeneration" (Letter) *Arch. Ophthalmol.* (Nov. 1992) vol. 110, p. 1517.

G. Walldius et al, "The Effects of Diet and Zinc Treatment on the Fatty Acid Composition of Serum Lipids and Adipose Tissue and on Serum Lipoproteins in Two Adolescent Patients with Acrodermatitis Enteropathica" *Am.J.Clin.Nutr.* (Oct. 1983) vol. 38, pp. 512–522.

P.A. Walravens, "Zinc Metabolism and its Implications in Clinical Medicine" *The Western Journal of Medicine* (Feb. 1979) vol. 130, pp. 133–142.

R.G. Weiner, "AIDS & Zinc Deficiency" (letter) *JAMA* (Sep. 21, 1984) vol. 252, No. 11, pp. 1409–1410.

C. Zapsalis et al, *Food Chemistry and Nutritional Biochemistry* John Wiley & Sons, New York (1985) pp. 1009, 1014, 1015, 1023.

Chemical Abstracts, vol. 116, No. 18, May 4, 1992; Abstract No. 181171 re HU 57 046 A (Hung.)–ORBAN, Gyula et al–"Roborant oral composition comprising vitamins, amino acids and trace elements".

Bogden J.D., et al. "Effects of One Year Supplementation with Zinc and Other Micronutrients on Cellular Immunity in the Elderly", *J. Am. Coll. Nutr.*, Jun. 1990; 9(3):214–225.

Casarett and Doull's *Toxicology: The Basic Science of Poisons*, McGraw–Hill, NY, 1996, pp. 715 and 721.

Greger J.L., et al. "Zinc, Nitrogen, Copper, Iron, and Manganese Balance in Adolescent Females Fed Two Levels of Zinc", *J. Nutr.*, Feb. 1978; 108:1449–1456.

Greger J.L. "Food, Supplements, and Fortified Foods: Scientific Evaluations in Regard to Toxicology and Nutrient Bioavailablility", *J. Am. Diet Assoc.*, Oct. 1987; 87(10):1369–73.

Mertz W. "Risk Assessment of Essential Trace Elements: New Approaches to Setting Recommended Dietary Allowances and Safety Limits", *Nutrition Reviews*, vol. 53, No. 7, pp. 179–185, 1995.

*Micromedex Inc.* 1998, Health Care Series vol. 97, "Drugdex Drug Evaluations, Zinc Salts" (Micromedex$^R$ Healthcare Series Integrated Index™ Search).

*Micromedex Inc.*, 1998, Health Care Series vol. 97, "Toxicologic Managements, Zinc Compounds" (Micromedex$^R$ Healtcare Series Integrated Index™ Search).

*Micromedex Inc.*, 1998, Health Care Series vol. 97, "Toxicologic Managements, Copper" (Micromedex$^R$ Healthcare Integrated Index™ Search).

Sandstead H.H. "Copper Bioavailability and Requirements", *Am. J. Clin. Nutr.*, Apr. 1982; 35:809–814.

Sandström B. "Toxicity Considerations When Revising the Nordic Nutrition Recommendations", *J. Nutr.*, Feb. 1998; 128(2 Suppl.):372S–374S.

Singh A., et al. "Exercise–Induced Changes in Immune Function: Effects of Zinc Supplementation", *J. Appl. Physiol.*, Jun. 1994; 76(6):2298–2303.

Yasui M., et al. *"Mineral and Metal Neurotoxicology"*, CRC Press, NY, 1997, pp. 5, 7–9.

FLAVORFUL ZINC COMPOSITIONS FOR ORAL USE INCORPORATING COPPER

FIELD OF INVENTION

This invention relates to zinc compositions for oral use. More particularly, this invention relates to compositions containing a zinc compound and a relatively lesser amount of a copper compound which when taken orally is palatable and without undesirable aftertaste. These compositions include, in addition to the zinc compound and copper compound, a base material and an amino acid.

BACKGROUND OF THE INVENTION

The value of nutritional supplements of elemental zinc is well established. Although zinc has been known to be essential for plant growth for more than a century, its essentially for the normal growth of animals was reported in 1934 and for man in 1963. Hypogonadism in males, skin changes, poor appetite, and mental lethargy are but some of the observable effects related to zinc deficiency in man. Carbonic anhydrase was the first metalloenzyme discovered in the 1930's. Today, approximately 100 enzymes, many of them essential to human well-being, have been found to contain zinc, and the evidence is strong that zinc is required for many (if not all) of these enzymes to express their activity. Several enzymes required for nucleic acid metabolism have been shown to require zinc. In this group are ribonucleic acid (RNA) and deoxyribonucleic acid (DNA) polymerases, deoxythymidine kinase, and reverse transcriptase. It has been shown experimentally that the activity of deoxythymidine kinase in rapidly regenerating connective tissue decreases as early as six days after animals are placed on a zinc-deficient diet. This metabolic defect resulting from nutritional zinc deficiency is an indication of the fundamental importance of zinc for cell division and protein synthesis.

Until recently, zinc deficiency in man was considered unlikely because of the widespread availability of zinc in nature. However, recent evidence suggests that nutritional zinc deficiency may be common among the people of many developing countries where they subsist on high cereal protein diets. Only recently has it been recognized that the phytate content of such diets severely restricts zinc availability, which translates nutritionally to markedly depressed zinc absorption in man under many practical circumstances. Marginal zinc deficiency may be widespread even in the United States because of self-imposed dietary restrictions, use of alcohol and cereal proteins, and the increasing use of refined foods which decrease the intake of trace elements. As meat is a major dietary source of zinc, vegetarians who consume cereals as a major source of protein may be in double jeopardy of zinc deficiency.

Therapeutically, zinc has a vital role in certain diseased or debilitated states. Zinc therapy is life saving in acrodermatitis enteropathica, a genetic disease caused by an autosomal recessive trait, which, although rare, had an extremely high mortality rate until it was discovered in 1973 that chronic administration of oral zinc salts was not only life saving but capable of lifetime control of the disease. Zinc supplementation markedly improves wound healing in zinc-deficient individuals. Zinc deficiency is an important feature in many cases of sickle cell anemia characterized by growth retardation and hypogonadism, and zinc appears to have a pharmacological anti-sickling effect. Zinc has also been shown to be beneficial in the relief of acute inflammatory conditions associated with rheumatoid arthritis.

The safety of zinc supplements in excess of the amounts found in a normal diet is well documented. Although excessive zinc produces toxic symptoms, such symptoms are rare. An acute dose of 2 g of zinc sulfate has been recommended as an emetic. Except for extremely large doses, zinc is non-toxic. Nevertheless, it has been established that the chronic ingestion of zinc in daily amounts in excess of about 100 mg, i.e. about seven times the recommended daily allowance (RDA) of zinc as a nutritional supplement, can in some individuals, result in the depression of blood levels of the beneficial form of circulating lipoprotein known as high-density lipoprotein (HDL). It is further known that the biochemical mechanism that is responsible for this effect is the competitive inhibition of the absorption of cupric ion, $Cu^{2+}$, from the gut by the presence therein of greater-than-normal amounts of zinc ion, $Zn^{2+}$. Both ions rely upon the intermediacy of the metallothionine protein for transport across the gut wall into the bloodstream. Although cupric ions interact more strongly with metallothionine than do zinc ions, the presence of a relatively large amount of zinc ions can suppress the absorption of cupric ions by direct competition for the available metallothionine. The ultimate effect of this competitive inhibition of the absorption of copper is the undesirable depression of circulating HDL because the cupric ion is an essential component of one of the enzymes in the series that synthesizes HDL in the body. It is further known that the inhibition of $Cu^{2}+$ absorption from the gut by $Zn^{2+}$ can be overcome if the individual who is ingesting the relatively large amounts of $Zn^{2+}$ co-ingests about one to two RDAs of $Cu^{2+}$. The RDA for copper is 2 milligrams. A modest increase in copper intake is effective because of the aforementioned greater affinity of cupric ion for metallothionine, relative to the affinity of zinc ion for metallothionine.

Until the present time, the more or less water-soluble zinc compounds such as the sulfate, chloride, acetate, gluconate, and the like, have been formulated as solid tablets or enclosed in gelatin capsules which are swallowed whole. Accordingly, the taste buds and other taste apparatus in the mouth and throat are not affected. These formulations generally dissolve in the gastric juice of the stomach and release zinc ions to be absorbed into the system via the stomach and intestines. It was found by a serendipitous observation of G. A. Eby, D. R. Davis, and W. W. Halcomb as reported in "Reduction in Duration of Common Colds by Zinc Gluconate Lozenges in a Double-Blind Study," *Antimicrobial Agents and Chemotherapy,* 25(1), pp. 20–24 (1984) that when modest quantities of zinc are slowly ingested by mouth so that the interior surfaces of the mouth and throat are intermittently bathed in a solution of ionic zinc, both the time course and the severity of the symptoms of the common cold are remarkably altered in a favorable way. Their double blind clinical study in 65 humans showed that allowing a tablet containing about 23 mg of elemental zinc, such as zinc gluconate, to slowly dissolve in the mouth once every two hours during 12 to 16 hours a day (the waking hours) reduced the duration of colds from 10.8 days in the untreated group to 3.9 days in the zinc-treated group; and at every time after about one day, the zinc-treated patients had a great reduction in cold symptoms compared to the patients who did not receive zinc. While the reported observations are highly significant both from the point of view of statistical validity and of the importance of these observations to public health, the authors stated repeatedly in their paper that the disagreeable taste of the zinc gluconate tablets was a serious problem. Many patients receiving zinc gluconate discontinued the treatment on the first day "due to objection to the treatment." The authors stated that "the zinc gluconate lozenges [tablets] we used caused an unexpected unpalatability and distortion of taste in many subjects . . . " and mentioned "the somewhat bitter aftertaste which some people report for zinc gluconate." Furthermore, "unpalatable taste," "distortion of taste," and "mouth irritation" were common objections.

The original observation of the efficacy of unflavored zinc gluconate tablets has received strong confirmation. Two large, double-blind, placebo-controlled clinical studies have been carried out and reported in the medical literature. The first was carried out at the Dartmouth College Cold Clinic in New Hampshire and reported by J. C. Godfrey, B. Conant Sloane, D. S. Smith, J. H. Turco, N. Mercer, and N. J. Godfrey in "Zinc gluconate and the common cold: A controlled clinical study," *Journal of International Medical Research*, 20(2), pp. 234–246 (1992). This study used sugar-based lozenges containing zinc gluconate equivalent to 23 mg of zinc, and glycine, prepared by serial dilution technology to produce a formulation according to U.S. Pat. No. 4,684,528 and U.S. Pat. No. 4,758,439. Participants in this study who met protocol requirements and who received active lozenges within two calendar days of the onset of cold symptoms and dissolved them in their mouths every 2 hours while awake, as specified in the protocol carried out under a U.S. Investigational New Drug Application, experienced colds that lasted only 58% (mean duration) as long as patients who received a placebo. Patients in this study who received the active medication also experienced significant reductions of symptom severity and duration as compared to those who received the placebo.

The second double-blind study was done at the Cleveland Clinic Foundation by S. B. Moussad, M. L. Macknin, S. V. Medendork, and P. Mason and reported in "Zinc gluconate lozenges for treating the common cold," *Annals of Internal Medicine*, 125(2), pp. 81–88 (1996). Patients who qualified for this study had cold symptoms for no more than 24 hours prior to entry. The study used zinc gluconate lozenges containing glycine, prepared in the same manner as for the Dartmouth study but containing just 13.3 mg of zinc. When the data from this study were analyzed on the same statistical basis as the Dartmouth study, i.e., using only the 83 out of 100 patients who met all criteria specified in the protocol, it was found that patients who took active medication had colds for only 52% as long as those who got a placebo. As in the Dartmouth study, patients in this study also experienced a rapid reduction in symptom severity, compared to those on a placebo.

As noted, zinc gluconate by itself has a very bad taste which may be overcome by formulations containing an excess of glycine or certain other selected amino acids such as described in U.S. Pat. Nos. 4,684,528 and 4,758,439. It has been found that nutritionally useful copper salts such as cupric gluconate, cupric sulfate, cupric acetate, and cupric chloride also have undesirable organoleptic properties by themselves or in admixture with zinc gluconate in proportions (e.g., 1/33 mole of cupric salt per mole of zinc salt) that are useful to prevent the aforementioned adverse effect on HDLs. Accordingly, in order to take advantage of the important effect of zinc upon the common cold while negating any potential adverse effect of zinc ingestion upon the high density lipoproteins of human beings it is necessary to develop a formulation or formulations of pharmaceutically acceptable zinc salts combined with a minor proportion of cupric salts which are palatable enough to be taken with the frequency necessary to suppress symptoms of the common cold.

Another reason for developing zinc formulations having acceptable taste is to permit an increased or prolonged oral dosage. As described above, it has been found that the ingestion of zinc as tablets or capsules which pass directly to the stomach before disintegrating is ineffective for providing a zinc supplement for certain applications, including the control of cold symptoms. When zinc-containing lozenges are dissolved orally for treating an average common cold, no affect has been shown to occur on HDLs. However, if a user decides to take the zinc-containing lozenges on a daily basis as a dietary supplement or to control respiratory allergies, or has numerous colds occurring close in time, such prolonged intake of zinc can affect HDLs.

PRIMARY OBJECTS AND GENERAL DESCRIPTION OF THE INVENTION

Accordingly, it is a primary object of the invention to provide a zinc supplement containing a minor molecular proportion of a copper supplement for oral usage which is palatable and which does not have a disagreeable aftertaste.

It is another primary object to provide a zinc supplement containing a minor molecular proportion of a copper supplement for oral usage which permits a large oral dosage in simple and convenient form, without adversely affecting HDLs.

These primary and other objects of the invention will be apparent from the following general description and the detailed examples.

According to the present invention, it has been found that compositions containing a zinc compound, a minor molecular proportion of a copper compound, a base material such as a candy or syrup, and certain amino acids in which the molecular ratio of amino acid to zinc is in the range of 2:20 are very pleasant to the taste and leave no undesirable aftertaste. The composition contains from about 1 mg to about 5 mg of zinc for each gram of the total composition. The copper compound is present in a molecular proportion to the zinc of from about 0.1 to about 0.01.

Amino acids which have been found useful for the purpose of this invention are glycine, L-alanine, D,L-alanine, L-2-aminobutyric acid, D,L-2-aminobutyric acid, L-valine, D,L-valine, L-isovaline, D,L-isovaline, L-leucine, D,L-leucine, D-isoleucine, D,L-isoleucine, L-lysine, and D,L-lysine. It has also been found that complexes between zinc and the named amino acids having the composition zinc(amino acid)$_2$ are water-soluble and have very good flavors when formulated with an excess of the same amino acid, excess being in the range of 2 to 20 moles of the amino acid per mole of zinc(amino acid)$_2$. It has further been found that certain other amino acids, such as aspartic and glutamic acids, are not useful for this purpose. Therefore, it has been found that it is not possible to predict which zinc and amino acid combination will have an acceptable taste unless it is prepared and tested.

Examples of complexes between zinc and an amino acid suitable for use in the invention include a zinc glycine complex having a formula Zn(C$_2$H$_4$NO$_2$)$_2$.nH$_2$O in which n has value of 1, 1.5, or 2, combined with from 1.8 to 7.1 parts by weight of anhydrous glycine; a zinc alanine complex having a formula of Zn(C$_3$H$_6$NO$_2$)$_2$.nH$_2$O in which n has a value of 0.5, 1 or 2, combined with from 1.8 to 7.1 parts by weight of anhydrous amino acid alanine; a zinc D,L-lysine complex having a formula of Zn(C$_6$H$_{13}$N$_2$O$_2$)$_2$.4H$_2$O combined with from 0.9 to 3.5 parts by weight of anhydrous glycine; a zinc L-leucine complex having a formula of Zn(C$_6$H$_{12}$NO$_2$)$_2$ and combined with from 1.1 to 4.6 parts by weight of anhydrous glycine; a zinc D,L-alpha-aminobutyric acid complex having a formula of $Zn(C_4H_8NO_2)_2$, combined with from 1.4 to 5.6 parts by weight of anhydrous glycine; and a zinc L-valine complex having a formula of $Zn(C_5H_{10}NO_2)_2$, combined with from 1.2 to 5.0 parts by weight of anhydrous glycine.

The zinc compound which can be used in combination with the amino acids noted above can be in any of the forms commonly used, such as the sulfate, chloride, acetate, gluconate, ascorbate, citrate, aspartate, picolinate, orotate and transferrin salts, as well as zinc oxide and complexes of divalent zinc with the amino acids. The minor proportion of the copper compound which can be used in combination with the zinc and amino acids noted above can be in any of the forms commonly used such as the sulfate, carbonate, chloride, acetate, gluconate, ascorbate, citrate, aspartate, picolinate, orotate and transferrin salts, as well as cupric oxide and complexes of divalent copper with the amino acids. It has been found, however, because of compatibility with the amino acids and the like, that the gluconate, citrate, and acetate salts of zinc and copper are preferred.

The base material which can be used as a carrier for the zinc compound containing a minor molecular proportion of a copper supplement and the selected amino acid can be a sweetening agent such as a soft or hard candy base; a syrup such as corn syrup; a gum material including chewing gums; or any other form which permits the oral intake of the zinc compound and particularly where the composition is retained in the mouth for a substantial period of time to permit prolonged contact in the mouth with the zinc to provide a slow release of zinc into the mouth. Preferably the base material is a hard or soft candy base optionally containing a flavoring agent such as a fruit flavor concentrate or a syrup such as a natural or artificially sweetened syrup.

The following examples of presently preferred embodiments serve to illustrate, but not to limit, the present invention.

PREPARATION OF HARD CANDY STOCK

A mixture of 400 g of sucrose, 160 ml of white corn syrup, and 160 ml of deionized water was heated to 212° F. while stirring in a one-liter Teflon-lined aluminum pan. When a clear solution was obtained, the mixture was heated without further stirring at the maximum rate possible without boil-over until the temperature of the mixture reached 300° F. The pale straw-colored product was poured in a 4 mm layer onto a lightly greased heavy aluminum pan. On cooling to room temperature the layer was fractured into convenient-sized pieces and stored in a sealed container. The yield was 522.9 g of product known in the art as "hard crack" caramel.

COMPOSITIONS WITH HARD CANDY AS BASE MATERIAL

Examples 1–7 illustrate hard candy bases containing from 2.31 to 4.67 mg of ionic zinc per gram of the composition and from 0.068 to 0.20 mg of cupric ion per gram of the composition.

EXAMPLE 1

Lemon-Flavored Zinc Gluconate Formulation 70 grams of hard candy stock was placed in a stainless steel (SS) pan and heated while stirring, to just thoroughly melt the stock. To this hot stock was added 5.510 g of a dry, finely-ground mixture containing 2.480 g of zinc gluconate trihydrate, 2.920 g of anhydrous glycine, and 0.110 g of cupric gluconate. The dry compound was evenly distributed in the melted stock by thorough mixing and, while the resulting mixture was still hot, 1.0 ml of natural lemon flavor concentrate was added and stirred in. The still-hot mixture was distributed among 24 lightly greased steel candy molds. The yield was 24 circular lozenges, average weight 2.6 g. The zinc content was 4.2 mg per gram and the copper content was 0.20 mg per gram.

A similar product containing no glycine had an unpleasant flavor and aftertaste.

EXAMPLE 2

Lemon-Flavored Zinc Acetate Formulation 70 grams of hard candy stock was placed in a stainless steel (SS) pan and heated while stirring, to just thoroughly melt the stock. To this hot stock was added 3.468 g of a dry, finely-ground mixture containing 0.780 g of zinc acetate dihydrate, 2.668 g of anhydrous glycine, and 0.020 g of cupric acetate monohydrate. The dry compound was evenly distributed in the melted stock by thorough mixing and, while the resulting mixture was still hot, 1.0 ml of natural lemon flavor concentrate was added and stirred in. The still-hot mixture was distributed among 24 lightly greased steel candy molds. The yield was 24 circular lozenges, average weight 2.6 g. The zinc content was 4.2 mg per gram and the copper content was 0.20 mg per gram.

A similar product containing no glycine had an unpleasant flavor and aftertaste.

EXAMPLE 3

Lemon-Flavored Zinc Citrate Formulation 20.000 grams of hard candy stock was placed in a stainless steel (SS) pan and heated while stirring, to just thoroughly melt the stock. To this hot stock was added 0.727 g of a dry, finely-ground mixture containing 0.200 g of zinc citrate dihydrate, 0.517 g of anhydrous glycine, and 0.010 g of cupric citrate hemihydrate. The dry compound was evenly distributed in the melted stock by thorough mixing and, while the resulting mixture was still hot, 0.25 ml of natural lemon flavor concentrate was added and stirred in. The still-hot mixture was distributed among 24 lightly greased steel candy molds. The final mixture was cooled in the pan and fractured into convenient-sized chunks for evaluation. The zinc content was 3.1 mg per gram and the copper content was 0.095 mg per gram.

A similar product containing no glycine had a sharp, unpleasant flavor and aftertaste.

EXAMPLE 4

Lemon-Flavored Zinc Glycine Complex Formulations
(a) Preparation of Zinc Glycine Complex A mixture of 4.0690 g, 0.0500 mole, of ultra-pure zinc oxide (ZnO), and 8.2577 g, 0.1100 mole of anhydrous glycine was heated to 190° F. in 75 ml of deionized water for 30 minutes in a boiling water bath. only a small amount of white substance remained insoluble. The solution was gravity-filtered while hot, the filter was washed with 5 ml of hot water, and the filtrate was chilled in an ice bath. The resulting crystalline precipitate was filtered off, washed with 60 ml of 91% isopropyl alcohol, and air dried for 12 hours at 150° F. The yield was 6.805 g.

Anal. calc'd. for zinc glycinate sesquihydrate: ZnO, 33.83%.

Anal. found: ZnO, 33.51%.

The complex between zinc and glycine is a known compound as described in "Glycinate Complexes of Zinc and Cadmium," B. W. Low, F. K. Hirshfield, and F. M. Richards, *J. Am. Chem. Soc.*, 81, 4412–4416 (1959); J. V. Dubsky and A. Rabas, *Spisy Vidavny Prevodovedeclsou Fakultou Masarykovy Univ.*, No. 123, 3–18 (1930); *Chem. Abstr.* 25, 26557 (1932); and "Complex Formation Between Metallic Cations and Proteins, Peptides, and Amino Acids," F. R. N. Gurd and P. F. Wilcox, *Adv. in Protein Chem.*, 11, 311–348 (1956).

(b) Lemon-Flavored Product Preparation 22.500 grams of hard candy stock was placed in a stainless steel (SS) pan and heated while stirring, to just thoroughly melt the stock. To this hot stock was added 0.792 g of a dry, finely-ground mixture containing 0.4000 g of zinc glycinate sesquihydrate, 0.3750 g of anhydrous glycine, and 0.0166 g of cupric sulfate pentahydrate. The dry compound was evenly distributed in the melted stock by thorough mixing and, while the resulting mixture was still hot, 0.25 ml of natural lemon flavor concentrate was added and stirred in. The mixture was cooled in the pan and then fractured into convenient-sized chunks. The zinc content was 4.67 mg per gram and the copper content was 0.182 mg per gram.

A similar product containing no glycine had an unpleasant flavor and aftertaste.

EXAMPLE 5

Lemon-Flavored Zinc Alanine Complex Formulations (a) Preparation of Zinc-Alanine Complex A mixture of 4.0690 g, 0.0500 mole, of ultra-pure zinc oxide (ZnO), and 8.909 g, 0.1000 mole of anhydrous D,L-alanine was heated to 190° F. in 75 ml of deionized water for 20 minutes in a boiling water bath. An appreciable amount of substance remained insoluble. The solution was gravity-filtered while hot, and the clear filtrate was diluted to a total volume of 170 ml with 91% isopropyl alcohol. On cooling to 25° F., a crystalline product formed. The crystalline precipitate was filtered off and air dried for 12 hours at 150° F. The yield was 4.897 g.

Anal. calc'd. for zinc D,L-alaninate hemihydrate: ZnO, 32.48%.

Anal. found: ZnO, 32.60%.

The complex between zinc and D,L-alanine is a known compound as described in "Chemotherapeutic Drugs Against Viruses. XXXIV. Antiviral Effects of Zinc Complexes on Japanese B Encephalitis Virus," S. Akihama and S. Toyoshima, *Chem. Pharm. Bull.* (Tokyo), 10, 1254–1257 (1962); and "Chelation of some Bivalent Metal Ions with Alanine and Phenylalanine," V. Simeon and A. O. Weber, *Croat. Chem. Acta*, 38, 161–167 (1966).

(b) Lemon-Flavored Product Preparation 20.500 grams of hard candy stock was placed in a stainless steel (SS) pan and heated while stirring, to just thoroughly melt the stock. To this hot stock was added 0.1355 g of a dry, finely-ground mixture containing 0.1350 g of zinc D,L-alaninate hemihydrate, 0.3750 g of anhydrous glycine, and 0.0055 g of cupric phosphate trihydrate. The dry compound was evenly distributed in the melted stock by thorough mixing and, while the resulting mixture was still hot, 0.25 ml of natural lemon flavor concentrate was added and stirred in. The mixture was cooled in the pan and then fractured into convenient-sized chunks. The zinc content was 2.31 mg per gram and the copper content was 0.116 mg per gram.

A similar product containing no glycine had an unpleasant flavor and aftertaste.

(c) Preparation of Product with Added Alanine

The same procedure was used to combine 21.600 g of hard candy stock, 0.1500 g of zinc D,L-alaninate hemihydrate, 0.0067 g of cupric tartrate trihydrate, and 0.5000 g of D,L-alanine. The resulting product contained 2.47 mg of zinc per gram and 0.072 mg of copper per gram. It had a pleasant taste, with no unpleasant aftertaste.

EXAMPLE 6

Lemon-Flavored Zinc L-leucine Formulations (a) Preparation of Zinc L-leucine Complex Anhydrous L-leucine, 5.2472 g, 0.0400 mole, was dissolved in 30 ml of deionized water and heated to 120° F. Ultra-pure zinc acetate dihydrate 4.3900 g, 0.0200 mole, was added in small increments over one hour, with stirring. The solution did not clear, so another 20 ml of water was added and the mixture was heated in a boiling water bath to 190° F. for an additional 2½ hours. Water was then added to a total volume of 75 ml, the mixture was heated again to 190° F. and gravity-filtered. The retained solid was dried at 150° F. for 12 hours, found to weigh 2.717 g, and was analyzed.

Anal. calc'd. for zinc L-leucinate monohydrate: ZnO, 24.98%.

Anal. found: ZnO, 25.46%.

The clear filtrate from this first product was diluted to 300 ml with 91% isopropyl alcohol. The resulting precipitate of white flakes was filtered off and dried. Before drying, a few of the flakes were found to be immediately soluble in a few drops of water. After drying for 12 hours at 150° F. the product, 1.1216 g, was no longer freely soluble in water.

Anal. Calc'd. for anhydrous zinc L-leucinate: ZnO, 26.45%.

Anal. found: ZnO, 26.51%.

The complex between zinc and L-leucine is a known compound as described in "Chemotherapeutic Drugs Against Viruses. XXXIV. Antiviral Effects of Zinc Complexes on Japanese B Encephalitis Virus," S. Akihama and S. Toyoshima, *Chem. Pharm. Bull.* (Tokyo), 10, 1254–1257 (1962).

(b) Lemon-Flavored Product Preparation 20.5000 grams of hard candy stock was placed in a stainless steel (SS) pan and heated while stirring, to just thoroughly melt the stock. To this hot stock was added 0.3005 g of a dry, finely-ground mixture containing 0.2930 g of anhydrous zinc L-leucinate, and 0.0075 g of cupric glycinate dihydrate. The dry compound was evenly distributed in the melted stock by thorough mixing and, while the resulting mixture was still hot, 0.25 ml of natural lemon flavor concentrate was added and stirred in. The mixture was cooled in the pan and then fractured into convenient-sized chunks. The zinc content was 2.82 mg per gram and the copper content was 0.092 mg per gram.

(c) Preparation of Product with Added Glycine

The same procedure was used to combine 21.6000 g of hard candy stock, 0.4170 g of anhydrous zinc L-leucinate, 1.3500 g of anhydrous glycine, and 0.0106 g of cupric glycinate dihydrate. The resulting product had a zinc content of 3.58 mg per gram and a copper content of 0.116 mg per gram.

EXAMPLE 7

Lemon-Flavored Zinc D,L-Lysine Complex Formulations (a) Preparation of Zinc D,L-lysine Complex A mixture of 2.035 g, 0.025 mole, of ultra-pure ZnO, 7.310 g, 0.050 mole of anhydrous D,L-lysine, and 25 ml of deionized water was heated and stirred at 190° F. for 20 minutes. The cloudy solution was gravity filtered and the filter was rinsed with another 20 ml of hot water. No indication of a precipitate appeared when the clear filtrate was cooled to 85° F., so 225 ml of 91% isopropyl alcohol was added. A layer of oil settled to the bottom of the beaker. On cooling at room temperature overnight, the oil crystallized. The white solid was filtered off and dried at 150° F. for 21 hours. Yield: 6.80 g.

Anal calc'd. for zinc D,L-lysinate tetrahydrate: ZnO, 19.02%.

Anal. found: ZnO, 19.15%.

The complex of zinc with D,L-lysine is a known compound as described in "Chemotherapeutic Drugs Against Viruses. XXXIV. Antiviral Effects of Zinc Complexes on Japanese B Encephalitis Virus," S. Akihama and S. Toyoshima, *Chem. Pharm. Bull.* (Tokyo), 10, 1254–1257 (1962).

(b) Lemon-Flavored Product Preparation 20.1000 grams of hard candy stock was placed in a stainless steel (SS) pan and heated while stirring, to just thoroughly melt the stock. To this hot stock was added 0.459 g of a dry, finely-ground mixture containing 0.450 g of zinc D,L-lysinate tetrahydrate, and 0.009 g of cupric salicylate tetrahydrate. The dry compound was evenly distributed in the melted stock by thorough mixing and, while the resulting mixture was still hot, 0.25 ml of natural lemon flavor concentrate was added and stirred in. The mixture was cooled in the pan and then fractured into convenient-sized chunks. The zinc content was 3.35 mg per gram and the copper content was 0.068 mg per gram.

(c) Preparation of Product with Added Glycine

The same procedure was used to combine 20.1000 g of hard candy stock, 0.450 g of zinc D,L-lysinate tetrahydrate, 1.180 g of anhydrous glycine, and 0.010 g of cupric salicylate tetrahydrate. The resulting product had a pleasant flavor and contained 3.16 mg of zinc and 0.071 mg of copper per gram.

Similar formulations having good to excellent palatability are prepared from the zinc complexes of D,L-alpha-aminobutyric acid, L-valine, D,L-valine, L-isoleucine, D,L-isoleucine, L-isovaline, D,L-isovaline, L-lysine, and L-alanine. Similar formulations prepared with the dibasic amino acid/zinc complexes of L-aspartic acid, D,L-aspartic acid, L-glutamic acid and D,L-glutamic acid were found to be highly unpalatable and to leave undesirable and persistant aftertaste.

COMPOSITIONS WITH CHEWING GUM AS BASE MATERIAL

EXAMPLE 8

Preparation of Spearmint-Flavored Chewing Gum Containing Zinc Gluconate, Copper Gluconate, and Glycine 64.000 g of spearmint gum was heated in a pyrex bowl at 250° F. for 20 minutes and 6.859 g of a finely-ground mixture of 2.750 g of zinc gluconate trihydrate, 4.050 g of anhydrous glycine, and 0.0594 g of cupric gluconate monohydrate was blended into it with a stainless steel spoon. The mixture cooled rapidly, but its temperature was maintained by giving it two bursts of 750 Watt microwave energy totaling 35 seconds during the blending process. When it was thoroughly blended, the mixture was allowed to cool to about 105° F. and rolled into a ⅛ inch sheet that was then cut up into sticks weighing 3.1 g. This product contained 4.98 mg of zinc and 0.11 mg of copper per gram. The flavor and consistency were excellent. Zinc is slowly released upon chewing, as shown by EDTA (ethylenediamine tetraacetic acid) titration of zinc ion in the saliva and by the typically astringent zinc mouth-feel, but the flavor remains pleasant and there is no unpleasant aftertaste.

The zinc supplement compositions obtained according to the present invention which include the select amino acids and a trace of select copper salts to provide a proper balance in humans using this supplement in general possess very pleasant flavors. Although the characteristic flavor and mouth-feel of the zinc ion is present, it is markedly and unexpectedly modified by the presence of select amino acids and is not degraded by the presence of trace copper salts, to the extent that the unpalatable taste, distortion of taste, and mouth irritation associated with, for example, unformulated zinc gluconate, are greatly reduced or eliminated. This permits the formulation of compositions which will release over an extended period of time substantial amounts of zinc ions locally in the mouth and throat as necessary for certain applications, including control of the common cold. For example, a lozenge having a hard candy base will release approximately 14 mg of zinc ion uniformly over about 20 minutes in an adult human having a normal amount of saliva produced under the stimulation of hard candy. As will be apparent, the amount of zinc ion which will be released can be controlled by the amount of zinc compound incorporated into the base material.

As will be apparent to one skilled in the art, various modifications can be made within the scope of the aforesaid description. Such modifications being within the ability of one skilled in the art form a part of the present invention and are embraced by the appended claims.

It is claimed:

1. A slow release composition for oral consumption comprising a base material uniformly containing a zinc compound, a mono-carboxylic amino acid, and a copper compound, wherein the molar ratio of the amino acid to zinc is about 2:20, the copper compound is present in a molecular proportion to the zinc of from about 0.1 to about 0.01, and the zinc is slowly and uniformly released as the composition is orally consumed.

2. A slow-release composition for oral consumption comprising a base material uniformly containing (1) a zinc compound, (2) an amino acid selected from a group consisting of glycine, L-alanine, D,L-alanine, L-2-aminobutyric acid, D,L-2-aminobutyric acid, L-valine, D,L-valine, L-isovaline, D,L-isovaline, L-leucine, D,L-leucine, D-isoleucine, D,L-isoleucine, L-lysine, and D,L-lysine; and (3) a copper compound, wherein said composition has a molar ratio of said amino acid to zinc of about 2:20, said copper compound is present in a molecular proportion to the zinc from about 0.1 to about 0.01, and said zinc is slowly and uniformly released as said composition is orally consumed.

3. A slow-release composition for oral consumption comprising a base material uniformly containing (1) a zinc compound, (2) an amino acid selected from a group consisting of glycine, L-alanine, D,L-alanine, L-2-aminobutyric acid, D,L-2-aminobutyric acid, L-valine, D,L-valine, L-isovaline, D,L-isovaline, L-leucine, D,L-leucine, D-isoleucine, D,L-isoleucine, L-lysine, and D,L-lysine; and (3) a copper compound selected from a group consisting of cupric L-alaninate, cupric carbonate, cupric chloride, cupric citrate, cupric gluconate, cupric glycinate, cupric oxide, cupric salicylate, cupric sulfate, and cupric tartrate, wherein said composition has a molar ratio of said amino acid to zinc of about 2:20, said copper compound is present in a molecular proportion to the zinc from about 0.1 to about 0.01, and said zinc is slowly and uniformly released as said composition is orally consumed.

4. The composition of claim 1, 2 or 3 wherein said amino acid is glycine.

5. The composition of claim 1, 2 or 3 wherein said zinc compound is a zinc salt in the form of a sulfate, chloride, acetate, gluconate, ascorbate, citrate, aspartate, picolinate, orotate, and transferrin salt.

6. The composition of claim 1, 2 or 3 wherein said zinc compound is a complex of divalent zinc with said amino acid.

7. The composition of claim 1, 2 or 3 wherein said zinc compound is zinc gluconate.

8. The composition of claim 1, 2 or 3 wherein said zinc compound is zinc acetate.

9. The composition of claim 1, 2 or 3 wherein said zinc compound is zinc citrate.

10. The composition of claim 6 wherein said zinc complex is a zinc glycine complex having a formula $Zn(C_2H_4NO_2)_2 \cdot nH_2O$ in which n has value of 1, 1.5, or 2, combined with from 1.8 to 7.1 parts by weight of anhydrous glycine.

11. The composition of claim 6 wherein said zinc complex is a zinc alanine complex having a formula of $Zn(C_3H_6NO_2)_2 \cdot nH_2O$ which in n has a value of 0.5, 1 or 2, combined with from 1.8 to 7.1 parts by weight of anhydrous amino acid alanine.

12. The composition of claim 6 wherein said zinc complex is a zinc D,L-lysine complex having a formula of $Zn(C_6H_{13}N_2O_2)_2 \cdot 4H_2O$ combined with from 0.9 to 3.5 parts by weight of anhydrous glycine.

13. The composition of claim 6 wherein said zinc complex is a zinc L-leucine complex having a formula of $Zn(C_6H_{12}NO_2)_2$ and combined with from 1.1 to 4.6 parts by weight of anhydrous glycine.

14. The composition of claim 6 wherein said zinc complex is a zinc D,L-alpha-aminobutyric acid complex having a formula of $Zn(C_4H_8NO_2)_2$, combined with from 1.4 to 5.6 parts by weight of anhydrous glycine.

15. The composition of claim 6 wherein said zinc complex is a zinc L-valine complex having a formula of $Zn(C_5H_{10}NO_2)_2$, combined with from 1.2 to 5.0 parts by weight of anhydrous glycine.

16. The composition of claim 1, 2 or 3 wherein the composition contains from about 1 mg to about 5 mg of zinc for each gram of the total composition.

* * * * *